(12) United States Patent
Tretiakov et al.

(10) Patent No.: US 6,940,948 B1
(45) Date of Patent: Sep. 6, 2005

(54) DIGITAL X-RAY SCANNING APPARATUS

(75) Inventors: Vjatcheslav Tretiakov, Novosibirsk (RU); Andrei Skok, Novosibirsk (RU); Markus Portmann, Inwil (CH); Albert Geisser, Ennetbürgen (CH)

(73) Assignee: DDI Direct Digital Imaging AG, Lucerne (CH)

( * ) Notice: Subject to any disclaimer, the term of this patent is extended or adjusted under 35 U.S.C. 154(b) by 9 days.

(21) Appl. No.: 10/019,323

(22) PCT Filed: May 29, 2000

(86) PCT No.: PCT/IB00/00725
§ 371 (c)(1),
(2), (4) Date: Jun. 7, 2002

(87) PCT Pub. No.: WO01/00092
PCT Pub. Date: Jan. 4, 2001

(30) Foreign Application Priority Data

Jun. 25, 1999 (EP) ............................................. 99112248

(51) Int. Cl.$^7$ .............................. G21K 5/10; H05G 1/02
(52) U.S. Cl. ........................ 378/146; 378/181; 378/189; 378/197
(58) Field of Search ................. 378/62, 98.8, 146–150, 378/167, 170, 181, 189, 195–197; 250/370.09, 370.11

(56) References Cited

U.S. PATENT DOCUMENTS

| 3,869,615 | A | * | 3/1975 | Hovver et al. ............... 378/146 |
|---|---|---|---|---|
| 4,024,403 | A | * | 5/1977 | Bernstein et al. ........... 378/177 |
| 4,179,100 | A | * | 12/1979 | Sashin et al. .......... 250/370.09 |
| 4,358,856 | A | * | 11/1982 | Stivender et al. ........... 378/167 |
| 4,363,128 | A | * | 12/1982 | Grady et al. ................. 378/181 |
| 4,894,855 | A | * | 1/1990 | Kresse ........................ 378/196 |
| 5,220,589 | A | * | 6/1993 | Gard ............................ 378/19 |
| 5,287,396 | A | * | 2/1994 | Stegehuis ................... 378/98.2 |
| 5,463,668 | A | * | 10/1995 | Kagaya ...................... 378/98.2 |
| 5,617,465 | A | * | 4/1997 | Bucher ........................ 378/146 |
| 5,986,278 | A | * | 11/1999 | Becker et al. ............... 250/580 |
| 6,152,598 | A | * | 11/2000 | Tomisaki et al. ............ 378/209 |
| 6,200,024 | B1 | * | 3/2001 | Negrelli ....................... 378/197 |
| 6,325,537 | B1 | * | 12/2001 | Watanabe .................... 378/197 |
| 6,382,832 | B1 | * | 5/2002 | Schwieker et al. .......... 378/196 |

* cited by examiner

*Primary Examiner*—Allen C. Ho
(74) *Attorney, Agent, or Firm*—Donald S. Dowden; Cooper & Dunham LLP

(57) ABSTRACT

In order to provide an improved X-ray imaging quality an X-ray detector (14) is equipped with means (13, 15) for orienting it towards an X-ray source (2) during a scan (8a, 8b, 27). Means (9, 10, z) for reorienting a housing (10) comprising the X-ray detector (14) and a conventional cassette holder (4) and detector positioning means (9–12) cooperate to receive an X-ray beam (26a) with improved collimation quality. Thus the detection efficiency is increased, the image resolution is enhanced, and the beam exposure of patients (5) can be minimized. Embodiments relate to a linear X-ray detector (14) designed for a serial readout of image pixels, a collimator (3, 3a, 3b) for both scanning and wide-perture X-ray imaging, and a supporting arm (9) carrying the X-ray source (2), collimator (3) and detector arrangement (17).

11 Claims, 7 Drawing Sheets

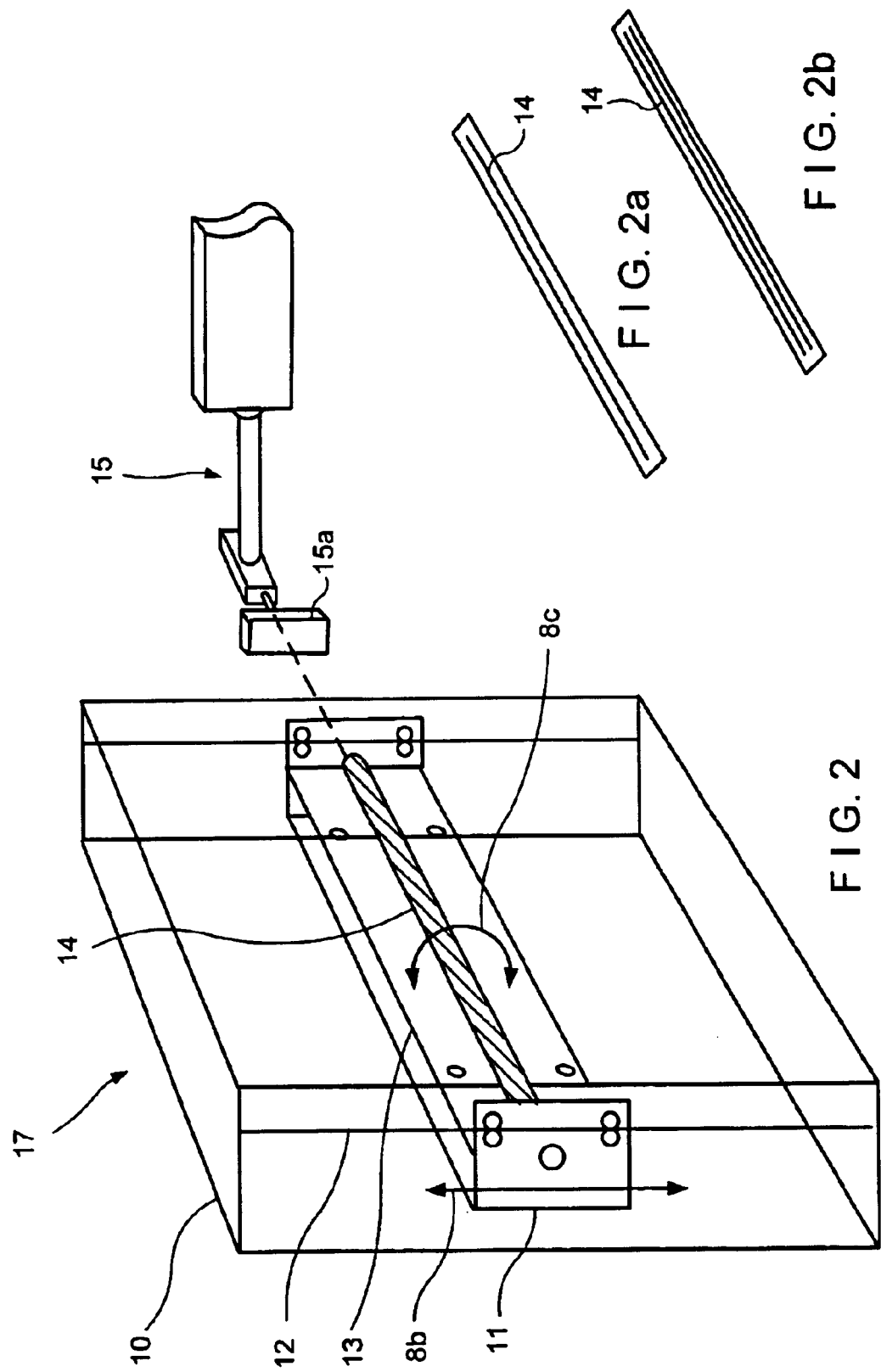

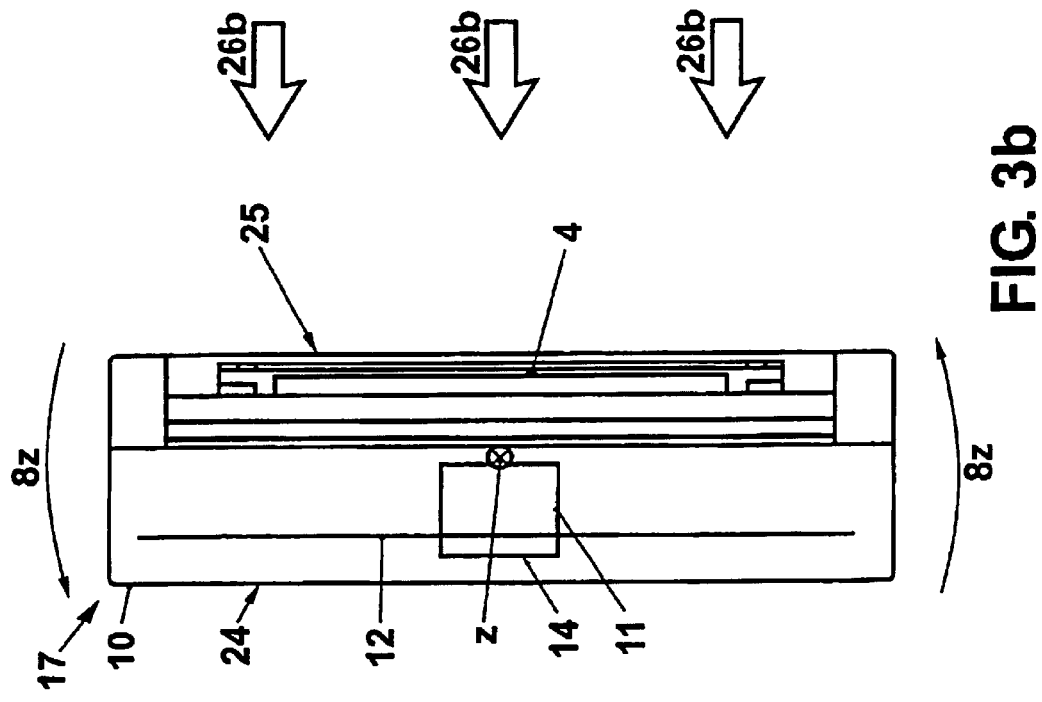
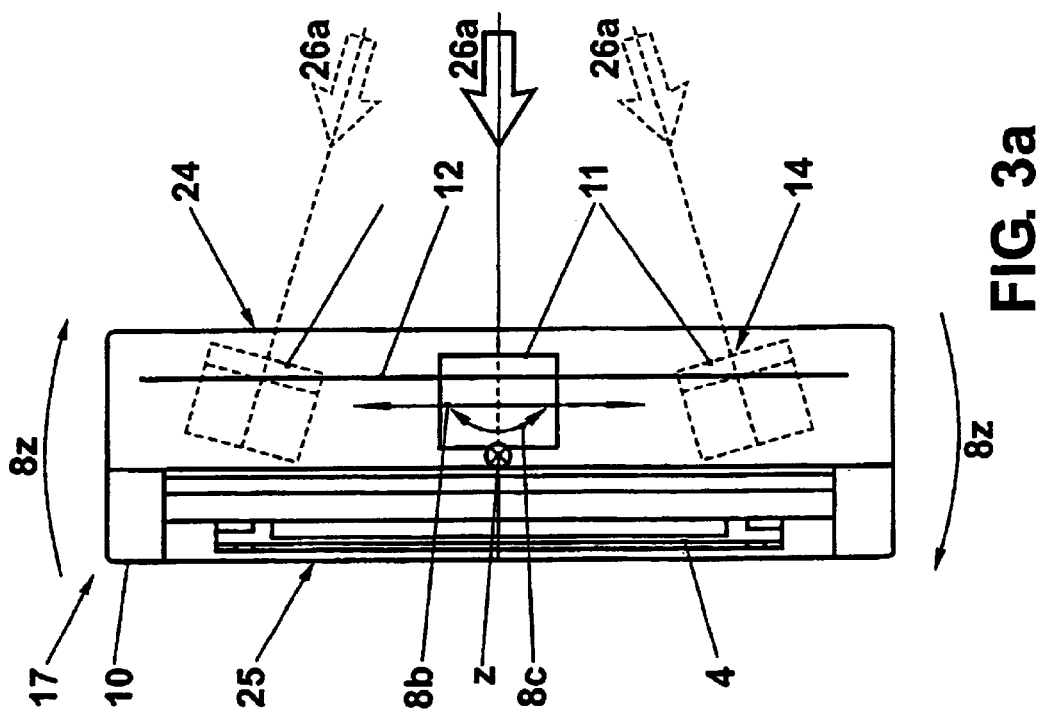

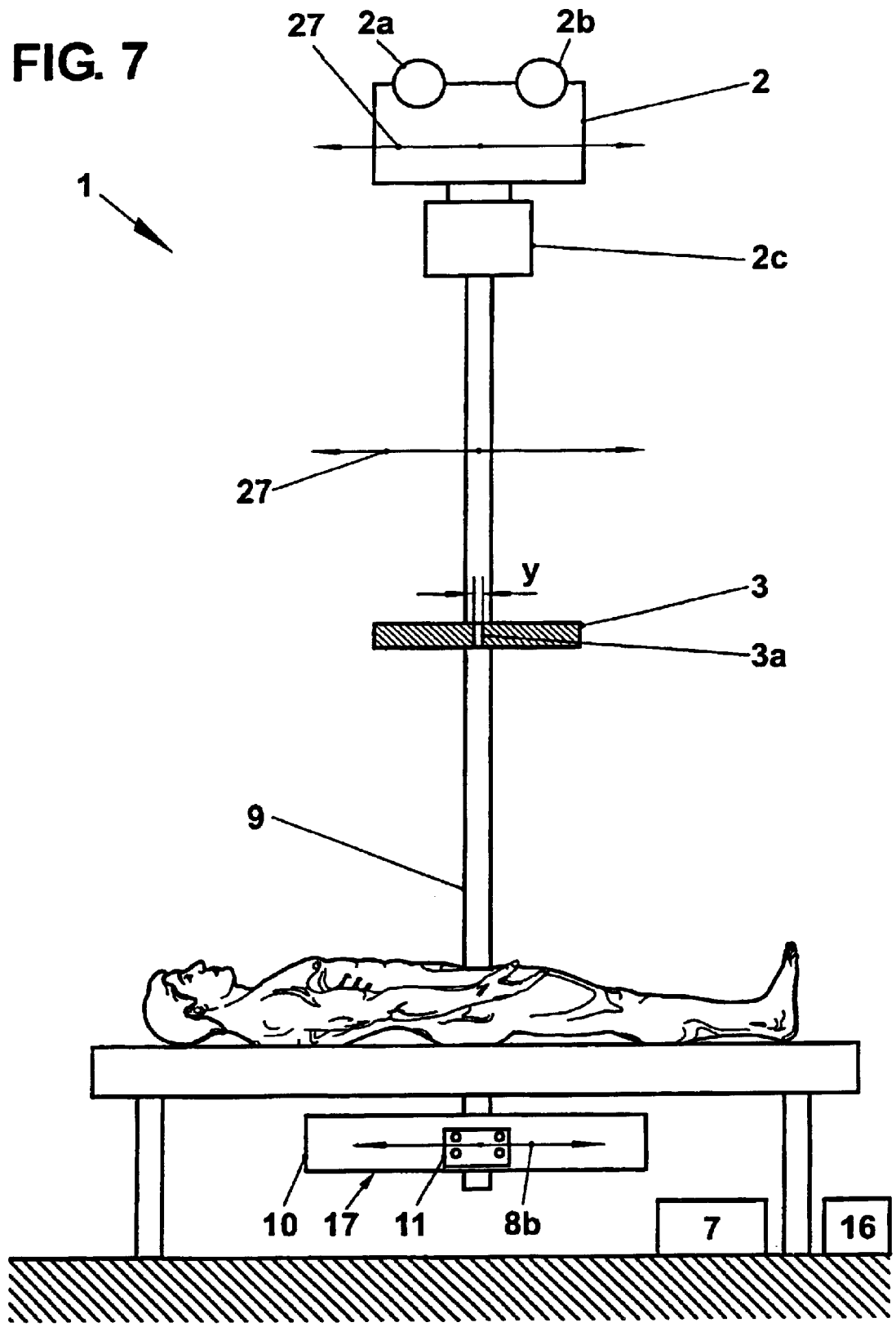

DIGITAL X-RAY SCANNING APPARATUS

CROSS REFERENCE TO RELATED APPLICATION

This application claims the priority of the European patent application No. 99112248.2, filed on Jun. 25, 1999, the disclosure of which is incorporated herein by reference in its entirety.

1. Technical Field

The invention refers to the field of X-ray imaging for medical and other purposes. It is based on the subject-matter as set forth in the preamble of the independent claims.

2. Background Art

The invention refers to a state of the art as known from the U.S. Pat. No. 4,773,087, in which a conventional photographic X-ray imaging system for full body or partial body imaging is disclosed. The system is equipped with a scanning digital detector for monitoring primary and scattered X-ray radiation. The laterally extended detector is positioned behind a film cassette and is addressed linewise and linearly shifted up and down for providing a two-dimensional scan of the film cassette area. The digital detector signal is used as a feedback signal for controlling the X-ray source in order to improve the photographic image quality.

However, the digital sensor by its own cannot deliver a useful X-ray image of the patient's body. The digital image quality, in particular the spatial resolution, scattering, dynamic range and sensitivity, is inappropriate for medical X-ray imaging. The disclosed digital scanning system shows insufficient performance in several respects: the detector is positioned in a rather large distance from the patient's body and behind the loaded film cassette, thereby enhancing X-ray scattering; the vertical scanning range of the detector is limited by a decrease of the effective aspect ratio and hence sensitivity when the detector is moved out of a position facing the X-ray source; as detector an image intensifier plate is proposed that suffers from low X-ray sensitivity and large optical scattering; furthermore the optical readout of the image intensifier plate is accomplished by a plurality of moving parts that add considerable mechanical complexity to the digital detector.

In the EP 0 291 299 a digital X-ray scanning system for partial or full body imaging is shown. A bar-shaped movable scintillator body and a multi-line photodetector are scanned synchronously with a moving X-ray beam across the stationary patient. The scan is performed by a linear translation of the detector arrangement and the collimator, which selects radiation from a wide-aperture X-ray source. A major problem is the fact that the patient cannot lean still at the X-ray apparatus, because the collimator in the front and the detector in the back of the patient are vertically moving. It is therefore difficult or impossible to maintain constant and reproducible distances collimator-patient and/or patient-detector during the scan. Furthermore, the patient must keep a certain (too large) minimal distance to the detector. Another problem is the loss of X-ray energy and the varying X-ray beam density or focus quality, that arise from using the wide-angle source and moving collimator. Consequently the overall image quality and in particular the spatial resolution are limited and are still considerably lower than in conventional photographic X-raying systems.

In the EP 0 904 734 a combined digital X-ray scanning and photographic system for panoramic dental X-ray imaging is disclosed. The X-ray source and the digital sensor cassette or film cassette are mounted on a rotary arm in fixed positions thereby facing each other. A panoramic x-ray image of teeth is generated by rotating the arm about a vertical axis centered at the patient's head and by sequentially reading out a vertical linear sensing array or by horizontally shifting a film cassette along a vertical collimator slit. Obviously X-ray imaging with a rotary movement is only feasible when scanning a head or other round body parts and preferentially small areas. The rotary movement is inadequate to scan longitudinally extended body parts, because the variations in imaging distance would by far exceed the depth of focus and blur the image. Therefore the system is incapable of producing full body images. Other disadvantages are, that the patient may not secure his head position by leaning to the rotary arm during a scan, and that the digital sensor cassette must be removed when a film cassette is mounted.

BRIEF SUMMARY OF THE INVENTION

It is the object of the invention to provide an improved digital X-ray system suitable for fast, large-area as well as high resolution X-ray imaging. This object is achieved according to the invention by the subject-matter as set forth in the independent claims.

The invention discloses novel means for orienting or positioning X-ray imaging means with respect to an X-ray source in order to achieve an improved X-ray imaging quality. More specifically, the invention resides in a special detector arrangement comprising a scanning X-ray detector, wherein an additional degree of freedom for reorienting the detector towards an X-ray source is provided, or wherein the detector housing further comprises a photographic plate and is reorientable for switching between digital scanning and high resolution photographic X-ray imaging, or wherein the digital scanning detector is positioned under an angle shifted towards an anode side of the X-ray tube in order to exploit an improved collimation quality of the X-ray beam. Thus, in the first aspect, the effective receiving area of the digital detector is increased, in the second aspect, the digital scanning is complemented by conventional high resolution imaging by providing mounting means for orienting either the digital detector or the photographic plate relative to the X-ray beam, and, in the third aspect, mounting means for orienting the digital detector are provided such that an X-ray beam can be received with minimum beam divergence. By these measures the detection efficiency is increased, the image resolution is enhanced and the beam exposure of patients can be minimized.

In the first aspect of the invention a digital X-ray scanning apparatus comprises an X-ray source, collimator, mounting and scanning means for a detector, digital data acquisition means and a control unit for steering the X-ray apparatus, wherein additional mounting and scanning means are provided for orienting the X-ray detector in at least one dimension towards the X-ray source independent from and in coordination with a digital scanning movement. Thus the detector efficiency is clearly improved. In particular the effective receiving area of the detector can be kept constant in at least one dimension even in extreme detector positions during the scan. By providing at least two separate degrees of freedom for the X-ray detector the scanning and orienting movements of the X-ray detector can be controlled and optimized independently from each other.

Embodiments refer to translational means for moving the X-ray detector on a linear path. By choosing a linear scanning movement along the patient's body the distance patient-detector can be kept constant which leads to a uniform and high image quality throughout the X-ray scan.

Alternatively the X-ray detector can be moved along a curved or circular path about the X-ray source such that the distance source-detector is kept constant. Rotational means for orienting the X-ray detector can be implemented such that an aspect ratio of the X-ray detector as viewed from the X-ray source is maintained throughout a scan. A single-line or few-or multi-line digital detector is well suited geometrically for linewise scanning an extended object such as a patient's body and serially reading out the detector in order to generate a two-dimensional image. As well, a single- or multi-line digital X-ray detector is advantageous over a large two-dimensional detector array since massive parallel data processing is avoided and only rather modest computing power is required.

In specific embodiments a carriage having a rotatable plate for receiving an elongated single- or multi-line x-ray detector is provided, wherein the carriage is movable in a direction essentially perpendicular to its lateral extension. In this set-up large area scans, as required for digital partial or full body X-ray imaging, can be realized with unprecedented image quality and little computing power. The means for scanning and orienting the X-ray detector can be mounted inside a housing that remains stationary during a scan. The patient can then lean to the housing in order to maintain a constant distance to the detector. Thereby the quality and repeatability of digital X-ray imaging is further improved.

Moreover, a swiveling mounting of the X-ray source, a mechanical or electrical coupling between the scanning and orienting movement of the X-ray detector and the swiveling or translational movement of the X-ray source, and sliding clutches for a safe operation of the apparatus may be provided.

In the second aspect of the invention a digital X-ray scanning apparatus comprises an X-ray source, collimator, mounting and scanning means for a detector, digital data acquisition means, a control unit for steering the X-ray apparatus and additional photographic X-ray imaging means including a cassette holder for photographic films, wherein a common housing is provided for receiving the X-ray detector and the cassette holder in such a way that they are facing towards different side faces of the housing, and the housing is reorientable such that either the film cassette or the X-ray detector is positioned for X-ray imaging. As a consequence, the X-ray detector and the cassette holder for photographic films are permanently installable in the X-ray apparatus. It is sufficient to reorient the common detector/cassette holder housing and to adapt the X-ray collimator in order to switch between digital and conventional X-ray imaging. There is no need to store either the detector or the film cassette in a separate place. Thus switching between digital and conventional X-ray imaging is strongly facilitated.

Moreover, the range of application of the digital X-ray scanning apparatus is favourably enlarged by integrating photographic X-ray imaging means in such a way. The digital subsystem serves for fast X-raying parts or the totality of a human or animal body or other extended object. Such X-ray scans may be monitored on a TV screen and/or may be image processed, stored, archived and retrieved electronically. By switching to the photographic subsystem specific body parts or object details can be investigated in greater detail and with higher resolution. The photographic subsystem is particularly useful for imaging bone structures and performing special examinations, such as mammography. The easy handling of both subsystems according to invention is of great advantage for medical personnel.

Embodiments refer to a housing which has the X-ray detector mounted on a front side and the cassette holder on a back side and which is rotatable such that either the front or back side is facing towards an X-ray source. Preferable implementations have any of the following features: the same X-ray source is utilized for digital and conventional X-ray imaging; the X-ray collimator is removable or openable for photographic X-ray imaging; and the removal or opening is steered automatically, e. g. by a sensor indicating the presence of a photographic film in the cassette holder, by a switch in the cassette holder, by a sensor indicating an orientation of the housing for either digital or photographic X-ray imaging, by means of software and/or by a manual switch.

In the third aspect of the invention a digital X-ray scanning apparatus comprises an X-ray source, collimator, mounting and scanning means for a detector, digital data acquisition means and a control unit for steering the X-ray apparatus, wherein mounting means for holding the X-ray detector in a position shifted towards an anode side of the X-ray source by an angle a are provided, wherein $0°<\alpha<\beta$ with $\beta$=anode angle. This detector orientation is specifically chosen to benefit from an improved X-ray beam quality and it allows to minimize the X-ray exposure of patients during digital X-ray scans.

In a preferred embodiment the positioning angle $\alpha$ is selected around $\beta/2$ and, in particular $4°<\alpha<12°$, preferably $\alpha=6°$ with $\beta=12°$.

Other embodiments relate to an integrated collimator design wherein the collimator is easily switchable between a collimated X-ray beam for digital X-ray scanning and a broad or wide-angle beam for conventional photographic X-ray imaging.

Further embodiments refer to the X-ray detector comprising a single- or multi-line array of scintillator crystals that are coupled to optical detectors, to an A/D converter and to a personal computer for serial readout.

A yet other embodiment addresses the dimensioning of the X-ray apparatus, in particular for fast digital full body imaging with improved image quality, by choosing appropriate distances source-detector, collimator-detector and patient-detector for adapting the beam shape to the digital detector dimensions and for minimizing X-ray scattering. Thereby digital imaging with image resolution better than 2 linepairs per mm is achievable with very low X-ray doses.

Final embodiments describe the design of a rotatable supporting arm for mounting an X-ray source with collimator and an X-ray detector, wherein the source plus collimator and the detector are individually tiltable and optionally the source-detector distance is variable.

Other objects, features and advantages of the present invention will become apparent from the dependent claims and the description in connection with the drawings.

BRIEF DESCRIPTION OF THE DRAWINGS

The description is related to the accompanying drawings, in which

FIGS. 2, 2a and 2b show embodiments of a first detector arrangement with a scanning and orienting mechanism suitable for large area digital X-ray imaging;

FIG. 3 shows a second detector arrangement that comprises a photographic plate and is reorientable for either digital or conventional X-ray imaging;

FIG. 7 shows an embodiment of the x-ray apparatus wherein an X-ray beam is aligned or scanned by translating a supporting arm.

In the drawings identical parts are designated by identical reference numerals.

DESCRIPTION OF THE PREFERRED EMBODIMENTS

Figure 1:
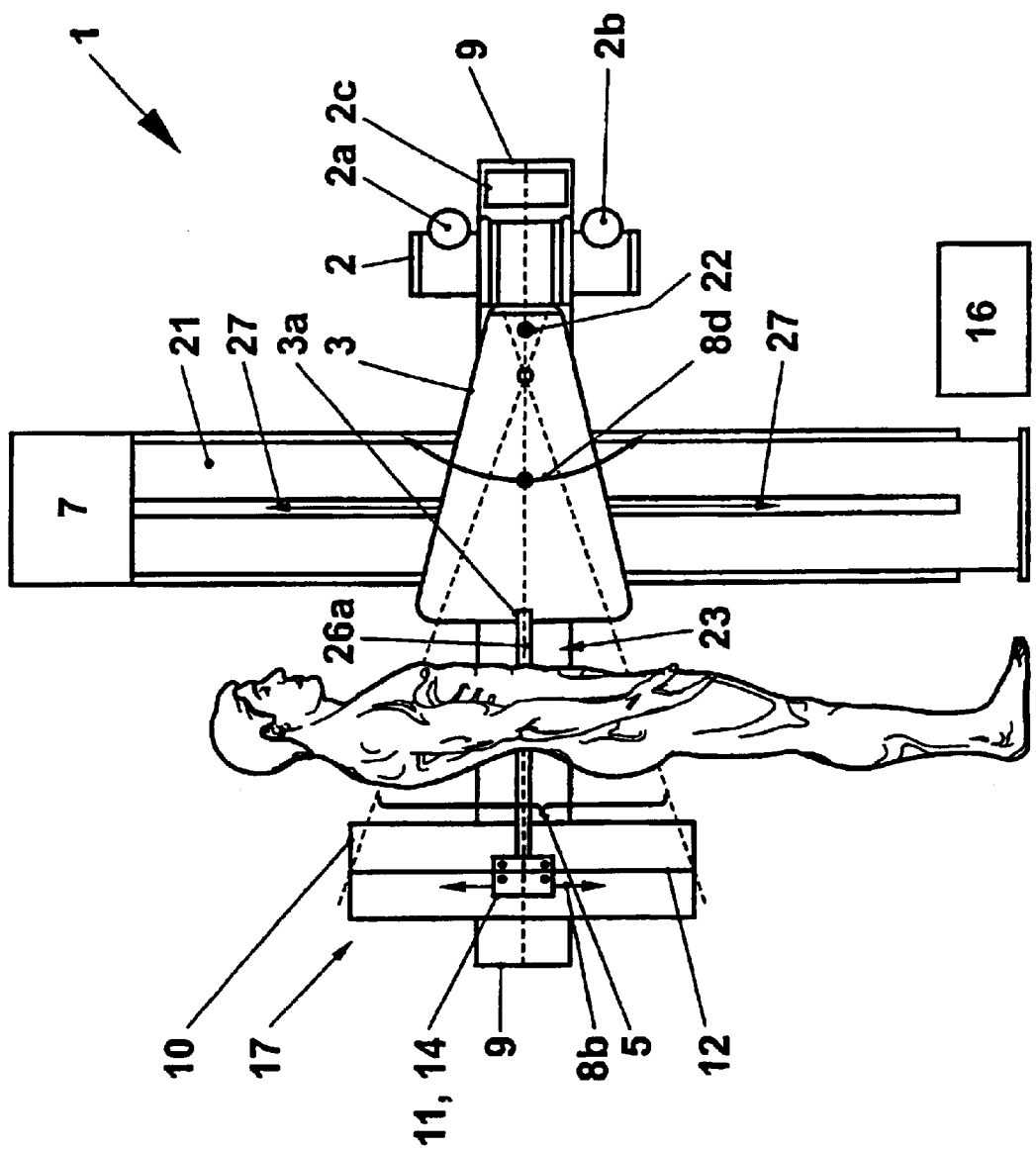
FIG. 1 shows a general schematic of a digital scanning X-ray apparatus comprising a detector arrangement according to invention.

The invention refers to an X-ray apparatus 1 as exemplified in FIG. 1. The apparatus 1 comprises an X-ray source 2 with an anode 2a and a cathode 2b (indicated schematically), a collimator 3 with a collimator silt 3a and an X-ray detector arrangement 17, a supporting arm 9 for holding the X-ray source 2 and the detector arrangement 17 and a structure or mount 21 for suspending the supporting arm 9. The detector arrangement 17 includes mounting and scanning means 10–12 for an X-ray detector 14. These means 10–12 comprise a detector housing 10 and a carriage 11 that is movable along guiding rails 12. The scanning means further comprise at least one motor 7. Means 16 for digital data acquisition from the X-ray detector 14 and a control unit 2c for steering the X-ray apparatus 1 are provided. A digital image of a patient's body is generated by scanning a collimated X-ray beam 26a over an area 5 and coordinately moving the carriage 11 with the detector 14 along a path 8b and/or 27. For this purpose the X-ray source 2 is swiveled, as indicated by arrows 8d, about a suspension point 22; alternatively it can be linearly translated (FIG. 7). The lateral extensions of the collimator slit 3a and of the detector 14 determine the width of the image to be scanned. However, it is also possible to perform a scanning movement of the X-ray source 2 and/or collimator slit 3a and the detector 14 in two dimensions. The supporting arm 9 may contain means 23 for driving moving parts 10, 11, 2, 3, 3a mounted to it. The supporting arm 9 itself can be shiftable, as indicated by arrows 27, along the structure 21. The orientation of the structure 21 and of the supporting arm 9 is adapted to the patient's position. Typically the structure 21 is vertical, when the patient is standing (as shown) or sitting, and it is horizontal, when the patient is lying. The supporting arm 9 can be oriented perpendicularly or otherwise tilted with respect to the structure 21.

FIG. 2 shows, in a first general aspect of the invention, additional mounting and scanning means 13, 15 for performing in at least one dimension an orienting movement 8c of the X-ray detector 14 towards the X-ray source 2 during a digital scanning procedure, wherein the orienting movement 8c and the scanning movements 8b and/or 27 are independent degrees of freedom of the X-ray detector 14, and the X-ray apparatus 1 is designed for steering the orienting movement 8c of the X-ray detector 14 in coordination with the scanning movement 8b and/or 27 of the X-ray detector 14. Sliding clutches 15a can be provided between the motor drive unit 15 and moving parts of the X-ray apparatus 1.

The mounting and scanning means 9–12, 7 shall comprise translational means 11, 12 for moving the X-ray detector 14 along a straight line segment 8b, 27 or along a curved or circular line segment inside the housing 10 or possibly together with the housing 10 (FIG. 6, arrows Ba); and/or the additional means 13, 15 comprise rotational means 13, 15 for tilting the X-ray detector 14 in order to maintain a constant aspect ratio of the X-ray detector 14 as viewed from the X-ray source 2; and/or the X-ray detector 14 is a single- or multi-line digital X-ray detector 14 useful for linewise scanning large areas 5.

The translational means 11 shown in FIG. 2 is a carriage 11 that is movable in a direction perpendicular to its lateral extension, the rotational means 13 is a rotatable plate 13 that is mounted on the carriage 11 and is designed for receiving the X-ray detector 14, and, in particular, the rotatable plate 13 is laterally extended for receiving an elongated single-line digital X-ray detector 14 suitable for partial or full body X-ray scanning 8a, 8b, 8d, 27. The plate 13 can be rotated by a motor drive unit 15 such that the X-ray detector 14 is oriented in one dimension towards the X-ray source 2 during a digital scanning movement 8b, 27.

In a preferred embodiment a housing 10 for receiving the translational and rotational means 11, 12, 13 is provided, which housing 10 can be kept motionless or stationary during the scanning procedure. In particular the mounting and scanning means 9–12, 7 comprise means 9, 7, such as the supporting arm 9 and the motor 7, for repositioning the housing 10 for different scanning procedures. Alternatively, the housing 10 can be moved itself during a scan. Thereby a combined scanning movement 8b, 27 in coordination with an orienting movement 8c of the detector 14 is implemented.

FIG. 3 shows, in a second general aspect of the invention, a detector arrangement 17 with combined digital/ photographic detection means 4, 14 for an X-ray apparatus according to FIG. 1. In this configuration additional photographic X-ray imaging means 2, 3, 4 comprising a cassette holder 4 for photographic films are provided.

According to invention the mounting means 9–11 comprise a housing 10 that is designed for receiving the X-ray detector 14 and the cassette holder 4 in such a way that the X-ray detector 14 and the photographic film are facing towards different side faces of the housing 10 and the mounting means 9–11 are designed for performing a reorienting movement 8z of the housing 10 such that either the film cassette 4 or the X-ray detector 14 is positioned for X-ray imaging. The housing 10 of the integrated photographic/digital detector 17 may be closed or may have open faces. This detector arrangement is very advantageous because the digital detector 14 and the cassette holder 4 are always at hand. Switching between the digital and conventional X-ray imaging mode is simplified a lot compared to state of the art devices. Besides that, the rotational switching between both detection means 14, 4 allows to return precisely to a previous position of the digital scanning detector 14 after photographic imaging.

In detail FIG. 3 shows a housing 10 that is adapted for receiving the X-ray detector 14 on a front side 24 and the cassette holder 4 on a back side 25, and the mounting means 9–11 have an axis z for rotating the front side 24 or the back side 25 of the housing 10 towards an X-ray source 2. Preferably the axis z is oriented horizontally or vertically, corresponding to whether FIG. 3 presents a top view or side view. A torque-free 'suspension of the housing 10 is possible by positioning the rotational axis z at the center of gravity of the combined detector housing 10. As shown in FIG. 3a the X-ray beam is collimated 26a when the detector 14 is oriented towards the X-ray source 2. The detector 14 can, but need not be equipped with the previously described means 9–12, 7, 13, 15 for a linear scanning movement 8b, 27 and a rotational orienting movement 8c. According to FIG. 3b a broad X-ray beam 26b is used when a photographic film in a conventional cassette holder 4 shall be exposed. Note that the film and cassette holder 4 are shown only schematically.

Preferred embodiments are related to any of the following features: a use of the same X-ray source 2 for both digital and photographic X-ray imaging; an X-ray collimator 3 that is removable or a slit 3a that is openable for photographic X-ray imaging; an X-ray collimator 3 or a slit 3a that is steered automatically, in particular by a sensor indicating the presence of a photographic film in the cassette holder 4, by a switch in the cassette holder 4, by a sensor indicating an orientation of the housing 10 for digital or photographic X-ray imaging, by a manual switch, and/or by means of software.

Figure 4:
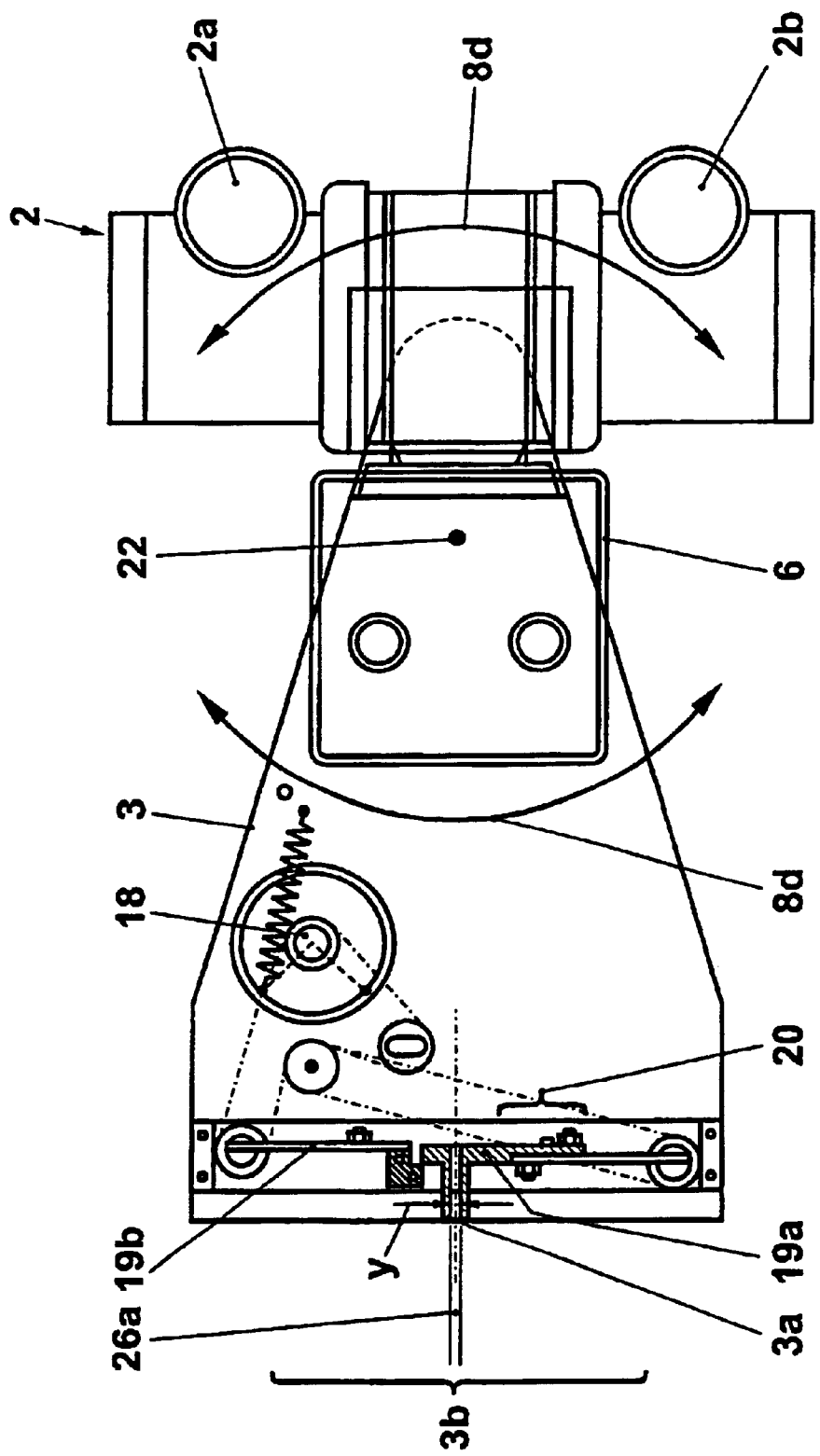
FIG. 4 shows an embodiment with an X-ray collimator that is switchable between a narrow and a wide aperture for digital and conventional X-ray imaging.

FIG. 4 shows a collimator 3 according to invention that is useful for both digital and photographic imaging. The essentially cone-shaped collimator 3 is rigidly attached to the X-ray source 2. The X-ray collimator 3 has an opening 3b for photographic imaging and comprises at least one movable shutter 19a with a built-in collimator slit 3a to provide a precisely collimated beam 26a for digital X-ray scanning. By this design a rectangular beam profile is provided that can easily and efficiently be widened or narrowed for photographic or digital imaging.

Desirable features are: an X-ray collimator 3 comprising one or two pivoted shutters 19a, 19b; an X-ray collimator 3 comprising a turning knob 18 to open or close the at least one shutter 19a, 19b; a shutter 19a having means 20 for adjusting a position of the slit 3a and/or a width y of the slit 3a in a range 0.2 mm <y <5 mm; and/or an X-ray collimator slit 3a that is positioned in a fixed distance from the X-ray source 2.

Preferably means for swiveling 8d the X-ray source 2 and the collimator 3, 3a in coordination with the scanning movement 8b, 27 and orienting movement 8c of the X-ray detector 14 are provided. In particular a balanced suspension about an axis 22 extending through the center of gravity of the X-ray source 2 and the collimator 3, 3a is provided for a torque-free swiveling movement 8d. As lo well, means for a rotational movement 8a (FIG. 6) or a linear movement 27 (FIG. 7) of the source 2 and collimator 3 in coordination with the movement 8b, 27, 8c of the detector 14 may be implemented. A counterweight for a force-free linear movement 8a would then be desirable. A hand grip 6 for swiveling and/or linearly shifting the source 2 and collimator 3 is shown as well.

A motor drive unit 15 and mechanical coupling means 23 are provided for synchronously driving the scanning movement 8b, 27 and the orienting movement 8c of the X-ray detector 14 and a translational or swiveling movement 27; 8a, 8d of the X-ray source 2 (FIGS. 1, 4, 6 and 7). The mechanical coupling means 23 can be e. g. a chain drive or a synchronous belt drive. These rather simple means allow for a high precision of synchronization between the at least two degrees of freedom 8b, 27; 8c of the detector 14 and the movement 27; 8a, 8d of the source 2 plus collimator 3, 3a. Alternatively several motor drive units 15 and an electrical control means 2c for driving and synchronizing the scanning movement 8b, 27 and the orienting movement 8c of the X-ray detector 14 and a translational or swiveling movement 27; 8a, 8d of the X-ray source 2 are provided. With such an electrical synchronization it is most simple to provide for a variable collimator-detector distance. For safety reasons sliding clutches can be built in between the at least one motor drive unit 15 and moving parts 2, 3, 4, 9, 10 of the X-ray apparatus 1.

Figure 5:
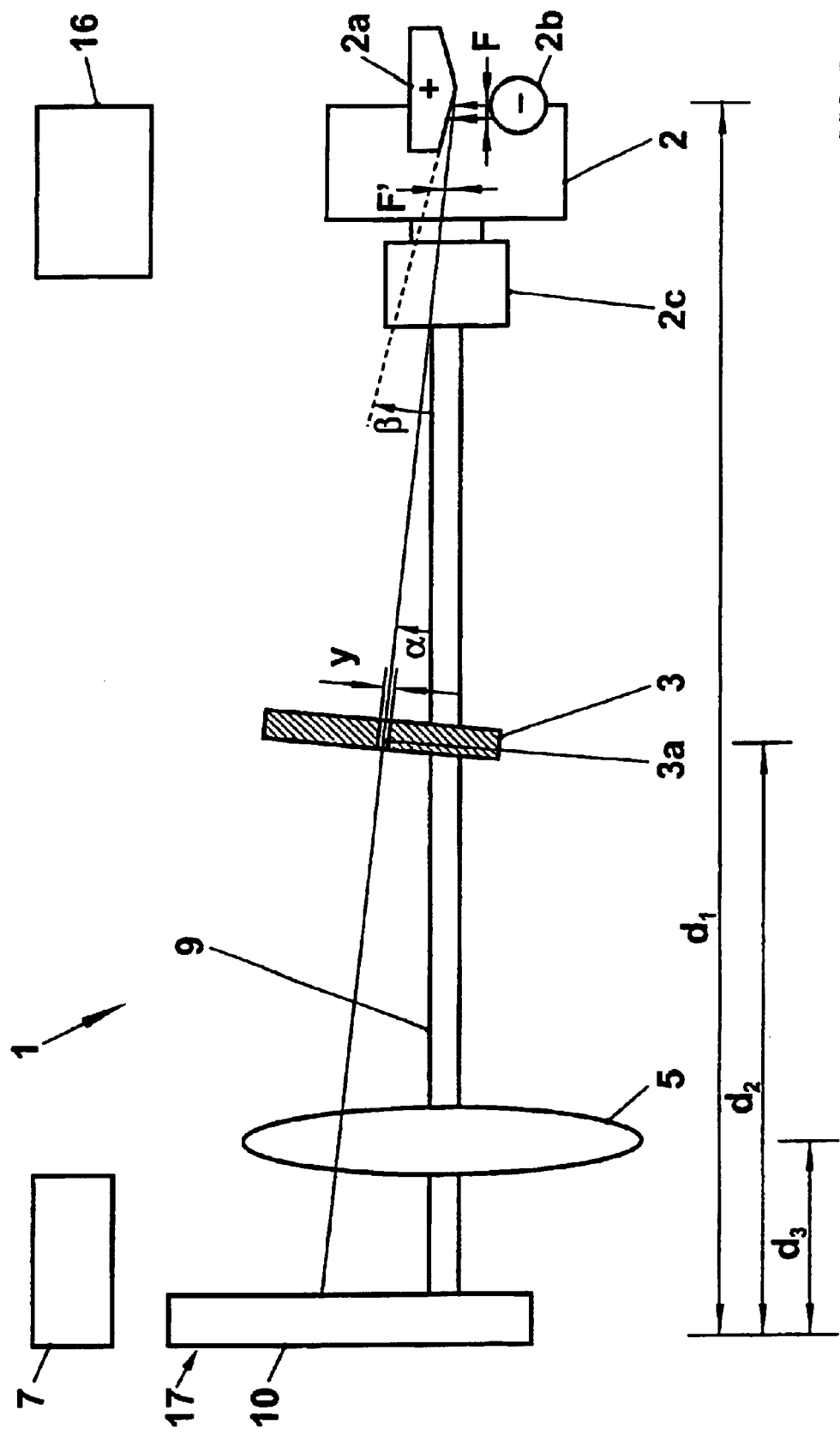
FIG. 5 shows a third detector arrangement wherein the position of a digital scanning detector is shifted by an angle towards an anode side of the X-ray tube.

FIG. 5 shows, in a general third aspect of the invention, a digital X-ray scanning apparatus 1, as known from FIG. 1, wherein the mounting means 9–11 are designed such that the X-ray detector 14 is held in a position shifted towards an anode side 2a of the X-ray source 2 by an angle α, where $0° < α < β$ with β=anode angle. Note that the anode 2a is shown in actual shape and orientation, but not to scale, whereas the cathode 2b is only indicated schematically. This detector orientation is chosen for receiving an X-ray beam with high collimation quality such that the X-ray dosage during the digital X-ray scan can be minimized.

The optimal choice of positioning angle a results, according to invention, from a trade off between emitted intensity and apparent focal spot size F'. The intensity emitted under anode angle β, i. e. tangentially to the anode surface, is considerably filtered and decreased, mainly owing to the surface roughness of the anode material. The intensity strongly increases for decreasing positioning angles $α < β$ and typically reaches 90% of its maximal value at a approximately equal to β/2. On the other hand the apparent focal size equals $F' = F \cdot \sin(β-α)/\sin(β)$ with F=actual focal spot size. F' is minimal, or ideally zero, for $α = β$ and increases with decreasing positioning angles $α < β$. Preferably the positioning angle shall be chosen around $α = β/2$ for receiving a high-intensity X-ray beam with focal spot size reduced by a factor 2. Conventional X-ray tubes 2 have anode target angles β between 12° and 16°. Consequently a useful range of positioning angles is $4° < α < 12°$, preferred $6° < α < 8°$, and most preferably $α = 6°$ when $β = 12°$ is assumed.

For the X-ray detector 14 a single- or multi-line X-ray detector 14 with X-ray sensitive elements (not shown) may be chosen. In particular the X-ray sensitive elements or pixels comprise scintillator crystals and optical detectors, that are connected to at least one A/D converter and to a microcomputer 16 for serial readout. By a careful choice of scintillators and detectors a high sensitivity can be achieved. A single- or multi-linear array is clearly superior to full image detectors that require enormous parallel computing power for readout. In contrast the invention takes advantage of a fast serial pixel readout that can be accomplished with commercially available personal computers. The serial readout is repeated linewise during the scanning process.

In further embodiments the single- or multi-line X-ray detector 14 has means for timing control of the single- or multi-line X-ray detector 14. The single- or multi-line X-ray detector 14 has means for gain and/or offset correction of analog signals from each pixel and/or from the whole single- or multi-line X-ray detector 14. With advantage the single- or multi-line X-ray detector 14 has a digital signal processor for detector control and data acquisition and/or it has a digital memory for data acquisition and data storage.

According to another embodiment the X-ray dosage and scattering radiation during digital X-ray scanning can be further reduced by an adequate choice of the geometrical beam parameters, such as apparent focal spot size F' of the X-ray source 2, collimator slit width y and distances $d_1$ between the X-ray source 2 (in particular its apparent focus) and the X-ray detector 14, $d_2$ between the X-ray collimator slit 3a and the X-ray detector 14 and $d_3$ between the patient 5 and the X-ray detector 14 (FIG. 5). The goals of an optimal parameter choice are: (i) fan beam width at detector site <pixel width (given by the width of the effective receiving area of the scintillator crystal); (ii) reduce half-shadow zones to diminish radiation passing by the detector 14; thereby the patient's X-ray exposure is further minimized; (iii) provide sufficient absolute intensity; and (iv) small patient-detector distance $d_3$ to reduce scattering from the X-rayed object.

Therefore a slit width y of the order of or smaller than the width of the receiving area of the scintillator crystal shall be chosen. The half-shadow zones result from the finite apparent focal spot size F' geometrically imaged through the collimator slit 3a. The intensity side lobes extending laterally over more than one pixel size are kept low by decreasing F', y and the image distance $d_2$. For providing enough absolute intensity the slit width y must be large enough. Finally the patient-detector distance $d_3$ shall be short.

Advantageously the X-ray apparatus 1 is dimensioned for full or partial body digital X-ray imaging. For this purpose and for a given pixel size (in particular width of effective receiving area of scintillator crystal) of 0.4 mm preferred parameter ranges are: slit width 0.2 mm <y <1.5 mm; overall distance 900 mm<$d_1$<1450 mm; image distance 500 mm<$d_2$<700 mm; and patient-detector distance 10 mm<$d_3$<200 mm.

Figure 6:
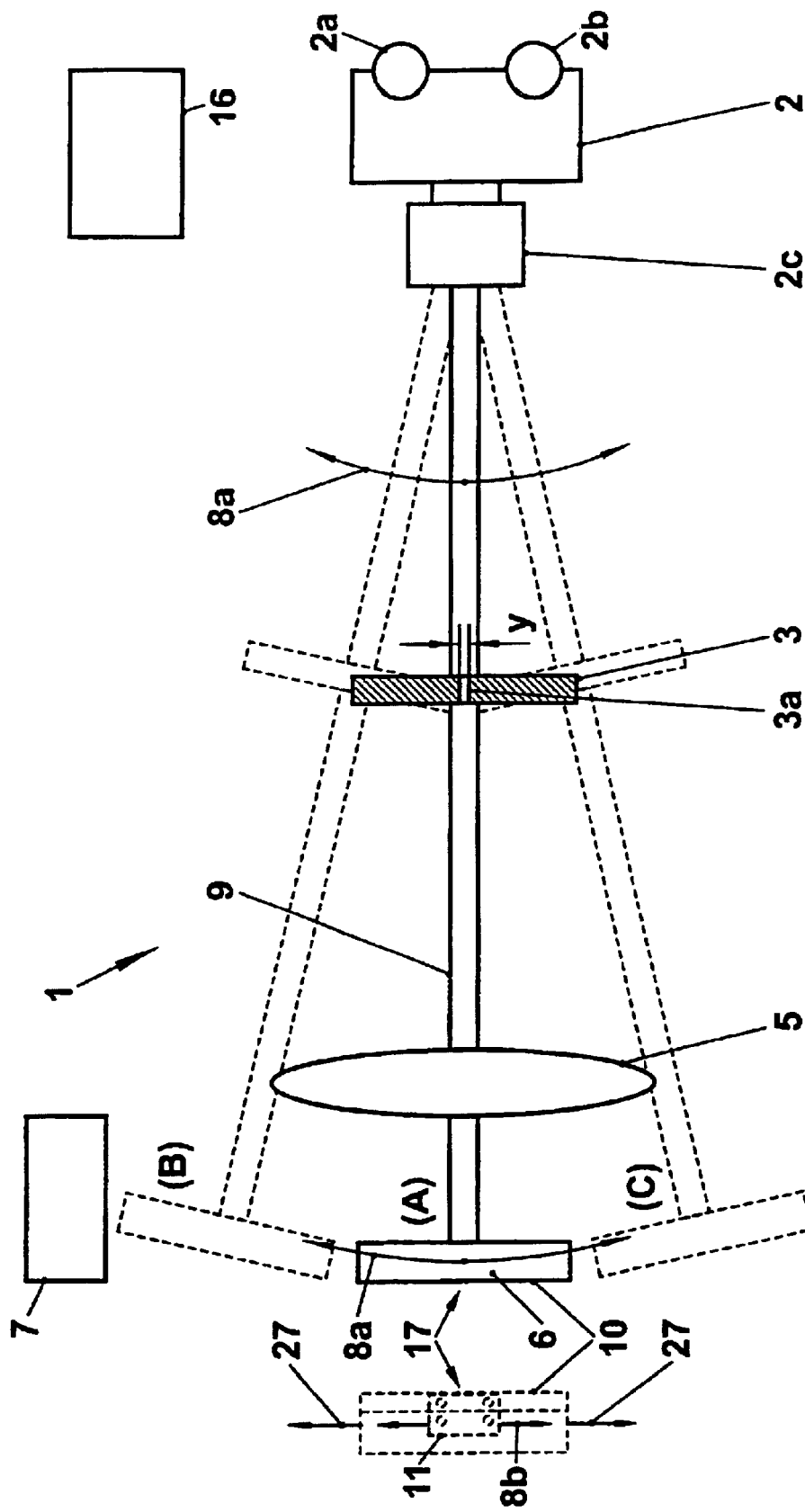
FIG. 6 shows an embodiment of the x-ray apparatus wherein an X-ray beam is aligned or scanned by swiveling a supporting arm.

FIGS. 1, 6 and 7 show the mechanical design and modes of movability of the X-ray apparatus 1 as a whole. The supporting arm 9 is adapted for carrying the X-ray source 2, the X-ray collimator 3 and the detector arrangement 17, according to invention, with the housing 10 comprising the X-ray detector 14. The supporting arm 9 itself shall be suspended in a rotatable fashion 8a. The X-ray source 2 together with the X-ray collimator 3 and the detector housing 10 are tiltable with respect to the supporting arm 9 in order to position the X-ray source 2, the X-ray collimator 3 and the detector 14 for X-raying a standing, sitting or lying patient 5.

Preferably the X-ray source 2 and/or the housing 10 for the X-ray detector 14 are movable along the supporting arm 9 for selecting a distance $d_1$ between the X-ray source 2 and the X-ray detector 14 or, in particular, a photographic film in a cassette holder 4 mounted in the housing 10.

FIG. 6 shows an example wherein the rotational or swiveling movement Ba of the supporting arm 9 is used to position and/or to scan the X-ray source 2 plus collimator 3 and the detector arrangement 17 with respect to the patient's body. The axis of rotation 8a may be located at the X-ray source 2, as shown, or may be shifted e.g. towards the patient 5. The transverse bar 9 in the middle position (A) (straight lines) is oriented horizontally or vertically depending on whether the patient 5 is standing/sitting or lying. The bar 9 may also be oriented under arbitrary angles relative to the patient 5. The dashed lines indicate the extreme positions (B), (C) of the swiveling movement 8a. Owing to the bar 9 the detector arrangement 17 containing the detector 14 (with or without cassette holder 4) and the X-ray collimator 3 travel coordinately on a circle segment. This motion might also be achieved using separate mountings for the detector arrangement 17 and collimator 3. Alternatively the detector arrangement 17 may be suspended independently and be movable along a straight line segment 27 and in coordination with the swiveling movement of the X-ray collimator 3 and X-ray source 2 or possibly the scanning movement 8b, 27 of the carriage 11. The movements 8a, 8b and 27 shall again be driven by at least one motor 7.

FIG. 7 shows an example wherein the supporting arm 9 has a suspension that is movable horizontally 27 for X-raying a lying patient 5. The detector arrangement 17 is movable 27 underneath the patient's body 5. In comparison, FIG. 1 shows a supporting arm 9 having a suspension that is movable vertically 27 for X-raying a standing or sitting patient 5. With advantage the supporting arm 9 is rotatable by at least 9° in order to switch between X-raying a standing or sitting and a lying patient 5.

The versatile movability of the supporting arm 9 is helpful for a fast alignment of the X-ray apparatus 1 with respect to the patient 5. Furthermore, a rotation 8a of the supporting arm 9 can be used to support or perform a swiveling movement 8d of the X-ray source 2 and/or of the detector arrangement 17. As well, a translation 27 of the supporting arm 9 can be used to support or perform a linear movement 27 of the X-ray source 2 and/or a scanning movement 8b of the detector 14.

In conclusion the invention discloses novel means 9–12, 7, 13, 15 for orienting or positioning X-ray imaging means 14, 4 with respect to an X-ray source 2 in order to achieve an improved X-ray imaging quality. According to invention a reorientable X-ray scanning detector 14, a reorientable combined scanning and photographic X-ray imaging means 14, 4 and means 9–12 for an improved detector positioning are provided. Thus the detection efficiency and image resolution are substantially increased. The new detector arrangement 17 is particularly useful for quick and efficient X-ray imaging of large areas 5 using digital or complementary conventional detection means 14, 4.

What is claimed is:

1. A digital X-ray scanning apparatus (1) comprising an X-ray source (2), an X-ray collimator (3), an X-ray detector (14), mounting means (9–11) for mounting the X-ray detector (14), scanning means (12, 7) for scanning (8b, 27) the X-ray detector (14) over an area (5), means (16) for digital data acquisition from the X-ray detector (14) and a control unit (2c) for steering the X-ray apparatus (1), wherein the mounting and scanning means (9–12, 7) comprise additional means (13, 15) for orienting (8c) the X-ray detector (14) in at least one dimension towards the X-ray source (2) during a digital scanning procedure, an orienting movement (8c) and a scanning movement (8b, 27) are independent degrees of freedom of the X-ray detector (14) and the X-ray apparatus (1) can steer the orienting movement (8c) of the X-ray detector (14) in coordination with the scanning movement (8b, 27) of the X-ray detector (14);

the mounting and scanning means (9–12, 7) comprise translational means (11, 12) for moving the X-ray detector (14) along a straight line segment (8b, 27) or along a curved or circular line segment, the additional means (13, 15) comprise rotational means (13, 15) for tilting (8c) the X-ray detector (14) in order to maintain a constant aspect ratio of the X-ray detector (14) as viewed from the X-ray source (2), and the X-ray detector (14) is a single- or multi-line digital X-ray detector (14);

characterized in that the translational means (11) is a carriage (11) that is movable in a direction perpendicular to its laterial extension, the rotational means (13) is a rotatable plate (13) that is mounted on the carriage (11) and receives the X-ray detector (14), and the rotatable plate (13) is laterally extended for receiving an elongated single-line digital X-ray detector (14) suitable for partial or full body X-ray scanning (8a, 8b, 27).

2. A digital X-ray scanning apparatus (1) comprising an X-ray source (2), an X-ray collimator (3), an X-ray detector (14), mounting means (9–11) for mounting the X-ray detector (14), scanning means (12, 7) for scanning (8b, 27) the X-ray detector (14) over an area (5), means (16) for digital data acquisition from the X-ray detector (14) and a control unit (2c) for steering the X-ray apparatus (1), wherein the mounting and scanning means (9–12, 7) comprise additional means (13, 15) for orienting (8c) the X-ray detector (14) in at least one dimension towards the X-ray source (2) during a digital scanning procedure, an orienting movement (8c) and a scanning movement (8b, 27) are independent degrees of freedom of the X-ray detector (14) and the X-ray apparatus (1) can steer the orienting movement (8c) of the X-ray detector (14) in coordination with the scanning movement (8b, 27) of the X-ray detector (14);

the mounting and scanning means (9–12, 7) comprise translational means (11, 12) for moving the X-ray detector (14) along a straight line segment (8b, 27) or along a curved or circular line segment, the additional means (13, 15) comprise rotational means (13, 15) for tilting (8c) the X-ray detector (14) in order to maintain a constant aspect ratio of the X-ray detector (14) as viewed from the X-ray source (2), and the X-ray detector (14) is a single- or multi-line digital X-ray detector (14); further comprising a housing (10) for receiving the translational and rotational means (11, 13), which housing (10) can be kept stationary during the scanning movement (8b, 27)

wherein the mounting and scanning means (9–12, 7) comprise means (9, 7) for repositioning the housing (10) for different scanning procedures.

3. A digital X-ray scanning apparatus (1) comprising an X-ray source (2), an X-ray collimator (3), an X-ray detector (14), mounting means (9–11) for mounting the X-ray detector (14), scanning means (12, 7) for scanning (8b, 27) the X-ray detector (14) over an area (5), means (16) for digital data acquisition from the X-ray detector (14) and a control unit (2c) for steering the X-ray apparatus (1), wherein the mounting and scanning means (9–12, 7) comprise additional means (13, 15) for orienting (8c) the X-ray detector (14) in at least one dimension towards the X-ray source (2) during a digital scanning procedure, an orienting movement (8c) and a scanning movement (8b, 27) are independent degrees of freedom of the X-ray detector (14) and the X-ray apparatus (1) can steer the orienting movement (8c) of the X-ray detector (14) in coordination with the scanning movement (8b, 27) of the X-ray detector (14);

characterized by means for swiveling (8d) the X-ray source (2) and the collimator (3, 3a) in coordination with the scanning movement (8b, 27) and orienting movement (8c) of the X-ray detector (14) and a balanced suspension of the X-ray source (2) and the collimator (3, 3a) for a torque-free swiveling movement (8d).

4. A digital X-rays canning apparatus (1) comprising an X-ray source (2), an X-ray collimator (3), an X-ray detector (14), mounting means (9–11) for mounting the X-ray detector (14), scanning means (12, 7) for scanning (8b, 27) the X-ray detector (14) over an area (5), means (16) for digital data acquisition from the X-ray detector (14) and a control unit (2c) for steering the X-ray apparatus (1), wherein the mounting and scanning means (9–12, 7) comprise additional means (13, 15) for orienting (8c) the X-ray detector (14) in at least one dimension towards the X-ray source (2) during a digital scanning procedure, an orienting movement (8c) and a scanning movement (8b, 27) are independent degrees of freedom of the X-ray detector (14) and the X-ray apparatus (1) can steer the orienting movement (8c) of the X-ray detector (14) in coordination with the scanning movement (8b, 27) of the X-ray detector (14);

characterized by a motor drive unit (15) and mechanical coupling means (23) for synchronously driving the scanning movement (8b, 27) and the orienting movement (8c) of the X-ray detector (14) and a translational or swiveling movement (27; 8a, 8d) of the X-ray source (2), wherein the X-ray apparatus has moving parts and sliding clutches are mounted between the at least one motor drive unit (15) and moving parts (2,3,4,9,10) of the X-ray apparatus (1).

5. A digital X-ray scanning apparatus (1) comprising an X-ray source (2), an X-ray collimator (3), an X-ray detector (14), mounting means (9–11) for mounting the X-ray detector (14), scanning means (12, 7) for scanning (8b, 27) the X-ray detector (14) over an area (5), means (16) for digital data acquisition from the X-ray detector (14) and a control unit (2c) for steering the X-ray apparatus (1), wherein the mounting and scanning means (9–12, 7) comprise additional means (13, 15) for orienting (8c) the X-ray detector (14) in at least one dimension towards the X-ray source (2) during a digital scanning procedure, an orienting movement (8c) and a scanning movement (8b, 27) are independent degrees of freedom of the X-ray detector (14) and the X-ray apparatus (1) can steer the orienting movement (8c) of the X-ray detector (14) in coordination with the scanning movement (8b, 27) of the X-ray detector (14);

comprising additional photographic X-ray imaging means (2, 3, 4) the X-ray apparatus further comprising a cassette holder (4) for photographic films, characterized in that the mounting means (9–11) comprise a housing (10) that receives the X-ray detector (14) and the cassette holder (4) in such a way that the X-ray detector (14) and the photographic film are facing towards different side faces of the housing (10) and the mounting means (9–11) perform a reorienting movement (8z) of the housing (10) such that either the cassette holder (4) or the X-ray detector (14) is positioned for X-ray imaging.

6. The X-ray apparatus (1) according to claim 5, characterized in that a) the housing (10) receives the X-ray detector (14) on a front side (24) and the cassette holder (4) on a back side (25) and the mounting means (9–11) has an axis (z) for rotating the front side (24) or the back side (25) of the housing (10) towards an X-ray source (2).

7. The X-ray apparatus (1) according to claim 5, characterized in that the X-ray collimator (3) is removable or a slit (3a) is openable for photographic X-ray imaging and the X-ray collimator (3) or the slit (3a) is steered automatically, by means selected from the group consisting of a sensor indicating the presence of a photographic film in the cassette holder (4), a switch in the cassette holder (4), a sensor indicating an orientation of the housing (10) for either digital or photographic X-ray imaging, a manual switch and software.

8. A digital X-ray scanning apparatus (1) comprising an X-ray source (2), an X-ray collimator (3), an X-ray detector (14), mounting means (9–11) for mounting the X-ray detector (14), scanning means (12, 7) for scanning (8b, 27) the X-ray detector (14) over an area (5), means (16) for digital data acquisition from the X-ray detector (14) and a control unit (2c) for steering the X-ray apparatus (1), wherein the mounting and scanning means (9–12, 7) comprise additional means (13, 15) for orienting (8c) the X-ray detector (14) in at least one dimension towards the X-ray source (2) during a digital scanning procedure, an orienting movement (8c) and a scanning movement (8b, 27) are independent degrees of freedom of the X-ray detector (14) and the X-ray apparatus (1) can steer the orienting movement (8c) of the X-ray detector (14) in coordination with the scanning movement (8b, 27) of the X-ray detector (14);

characterized by distance ranges 900 mm<$d_1$<1450 mm, 500 mm <$d_2$<900 mm and 10 mm<$d_3$<200 mm for full or partial body digital X-ray imaging, where $d_1$=distance between the X-ray source (2) and the X-ray detector (14), $d_2$=distance between the X-ray collimator slit (3a) and the X-ray detector (14) and $d_3$=distance between the patient (5) and the X-ray detector (14).

9. A digital X-ray scanning apparatus (1) comprising an X-ray source (2), an X-ray collimator (3), an X-ray detector (14), mounting means (9–11) for mounting the X-ray detector (14), scanning means (12, 7) for scanning (8b, 27) the X-ray detector (14) over an area (5), means (16) for digital data acquisition from the X-ray detector (14) and a control unit (2c) for steering the X-ray apparatus (1), wherein the mounting and scanning means (9–12, 7) comprise additional means (13, 15) for orienting (8c) the X-ray detector (14) in at least one dimension towards the X-ray source (2) during a digital scanning procedure, wherein an orienting movement (8c) and a scanning movement (8b, 27) are independent degrees of freedom of the X-ray detector (14) and the X-ray apparatus (1) can steer the orienting movement (8c) of the X-ray detector (14) in coordination with the scanning movement (8b, 27) of the X-ray detector (14);

characterized in that a supporting arm (9) carries the X-ray source (2), the X-ray collimator (3) and a housing (10) for the detector (14) and the supporting arm (9) is rotatable and the X-ray source (2) together with the X-ray collimator (3) and the housing (10) forth detector(14) are tiltable with respect to the supporting arm (9) in order to position the X-ray source (2), the X-ray collimator (3) and the detector (14) for X-raying a standing, sitting or lying patient (5).

10. The X-ray apparatus (1) according to claim 9, characterized in that the X-ray source (2) or the housing (10) for the X-ray detector (14) is movable along the supporting arm (9) for selecting a distance $d_1$ between the X-ray source (2) and the X-ray detector (14) or a photographic film in a cassette holder (4) contained in the housing (10).

11. The X-ray apparatus (1) according to claim 9, characterized in that the supporting arm (9) has a suspension that is movable horizontally (27) for X-raying a lying patient, the supporting arm (9) has a suspension that is movable vertically (27) for X-raying a standing or sitting patient, and the supporting arm (9) is rotatable by at least 90° in order to switch between X-raying a standing or sitting and a lying patient (5).

* * * * *